(12) United States Patent
Kang et al.

(10) Patent No.: US 12,338,200 B2
(45) Date of Patent: Jun. 24, 2025

(54) AMMOXIDATION CATALYST FOR PROPYLENE, MANUFACTURING METHOD OF THE SAME CATALYST, AMMOXIDATION METHOD USING THE SAME CATALYST

(71) Applicant: LG CHEM, LTD., Seoul (KR)

(72) Inventors: Kyungyeon Kang, Daejeon (KR); Ji Yeon Kim, Daejeon (KR); Jun Seon Choi, Daejeon (KR)

(73) Assignee: LG CHEM, LTD., Seoul (KR)

( * ) Notice: Subject to any disclaimer, the term of this patent is extended or adjusted under 35 U.S.C. 154(b) by 679 days.

(21) Appl. No.: 17/292,566

(22) PCT Filed: Sep. 25, 2020

(86) PCT No.: PCT/KR2020/013098
§ 371 (c)(1),
(2) Date: May 10, 2021

(87) PCT Pub. No.: WO2021/066410
PCT Pub. Date: Apr. 8, 2021

(65) Prior Publication Data
US 2022/0002233 A1 Jan. 6, 2022

(30) Foreign Application Priority Data

| Sep. 30, 2019 | (KR) | 10-2019-0121172 |
| Oct. 25, 2019 | (KR) | 10-2019-0134089 |
| Sep. 24, 2020 | (KR) | 10-2020-0123874 |

(51) Int. Cl.
*B01J 21/08* (2006.01)
*B01J 23/00* (2006.01)
(Continued)

(52) U.S. Cl.
CPC .............. *C07C 253/26* (2013.01); *B01J 21/08* (2013.01); *B01J 23/002* (2013.01);
(Continued)

(58) Field of Classification Search
CPC ...... B01J 21/08; B01J 23/002; B01J 23/8876; B01J 35/40; B01J 37/0213; B01J 37/04; B01J 37/082; C07C 253/26
See application file for complete search history.

(56) References Cited

U.S. PATENT DOCUMENTS 3,766,092 A * 10/1973 Honda et al. .......... B01J 27/192
558/324
4,052,332 A * 10/1977 D'Amore ............... B01J 27/285
502/25
(Continued)

FOREIGN PATENT DOCUMENTS

| CA | 805705 A | 2/1969 |
| CN | 1744949 A | 3/2006 |

(Continued)

OTHER PUBLICATIONS

Wenxing, et al. "Industrial Catalysis," Beijing: Chemical Industry Press, p. 223, Dec. 1978.
(Continued)

*Primary Examiner* — Cam N. Nguyen
(74) *Attorney, Agent, or Firm* — BRYAN CAVE LEIGHTON PAISNER LLP

(57) ABSTRACT

Provided is an ammoxidation catalyst for propylene, a manufacturing method of the same, and an ammoxidation method of propylene using the same. Specifically, according to one embodiment of the invention, there is provided a catalyst having a structure in which metal oxide is supported on a silica carrier, having narrow particle size distribution, and having excellent attrition loss. The catalyst may have a
(Continued)

D50 particle diameter of 30 to 300 μm, and D10 particle diameter, D50 particle diameter and D90 particle diameter may satisfy the relationship (D90−D10)/D50<2.0. The catalyst may have a chemical formula $Mo_{12}Bi_aFe_bCo_cK_dO_x$, where a is 0.1 to 5, b is 0.1 to 5, c is 0.01 to 10, d is 0.01 to 2, and x is 24 to 48.

15 Claims, 1 Drawing Sheet

(51) Int. Cl.
    *B01J 23/887*     (2006.01)
    *B01J 35/40*      (2024.01)
    *B01J 37/02*      (2006.01)
    *B01J 37/04*      (2006.01)
    *B01J 37/08*      (2006.01)
    *C07C 253/26*     (2006.01)

(52) U.S. Cl.
    CPC .......... *B01J 23/8876* (2013.01); *B01J 35/40* (2024.01); *B01J 37/0213* (2013.01); *B01J 37/04* (2013.01); *B01J 37/082* (2013.01)

(56) References Cited

U.S. PATENT DOCUMENTS

| | | |
|---|---|---|
| 4,123,453 A | 10/1978 | Grasselli et al. |
| 4,156,660 A | 5/1979 | Grasselli et al. |
| 4,176,234 A | 11/1979 | Grasselli et al. |
| 4,182,907 A | 1/1980 | Grasselli et al. |
| 4,259,211 A | 3/1981 | Krabetz et al. |
| 4,264,476 A | 4/1981 | Umemura et al. |
| 4,280,929 A | 7/1981 | Shaw et al. |
| 4,290,922 A * | 9/1981 | Umemura ............ B01J 23/8877 558/324 |
| 4,298,763 A | 11/1981 | Engelbach et al. |
| 4,374,759 A * | 2/1983 | Khoobiar ................. C07C 45/37 502/249 |
| 4,382,880 A | 5/1983 | Derrien |
| 4,388,223 A | 6/1983 | Ferlazzo et al. |
| 4,388,226 A | 6/1983 | Derrien et al. |
| 4,418,007 A | 11/1983 | Derrien |
| 4,479,013 A * | 10/1984 | Khoobiar ................. C07C 45/37 568/477 |
| 4,503,001 A | 3/1985 | Grasselli et al. |
| 4,541,964 A | 9/1985 | Katsumata et al. |
| 4,590,173 A | 5/1986 | Sasaki et al. |
| 4,609,635 A * | 9/1986 | Canavesi ............... C07C 253/26 502/212 |
| 4,767,878 A | 8/1988 | Grasselli et al. |
| 4,863,891 A | 9/1989 | Grasselli et al. |
| 5,093,299 A | 3/1992 | Suresh et al. |
| 5,175,334 A * | 12/1992 | Suresh ................... B01J 27/192 558/324 |
| 5,212,137 A * | 5/1993 | Suresh ................. B01J 23/8878 502/215 |
| 5,602,280 A | 2/1997 | Nagai et al. |
| 5,658,842 A | 8/1997 | Midorikawa et al. |
| 5,663,113 A * | 9/1997 | Midorikawa ........ B01J 23/8876 502/316 |
| 5,728,894 A | 3/1998 | Nagano et al. |
| 5,780,664 A * | 7/1998 | Aoki ................... B01J 23/8876 502/259 |
| 6,143,690 A | 11/2000 | Komada et al. |
| 6,245,931 B1 | 6/2001 | Aoki et al. |
| 6,458,742 B1 * | 10/2002 | Paparizos ............. C07C 253/26 502/300 |
| 6,509,508 B2 | 1/2003 | Kimura et al. |
| 6,525,217 B1 | 2/2003 | Unverricht et al. |
| 6,545,177 B2 | 4/2003 | Tanimoto et al. |
| 6,723,869 B1 * | 4/2004 | Mori ................... B01J 23/8876 558/324 |
| 6,781,013 B2 | 8/2004 | Tanimoto |
| 6,784,134 B2 | 8/2004 | Kasuga et al. |
| 6,797,839 B1 | 9/2004 | Hibst et al. |
| 6,818,702 B1 | 11/2004 | Orikabe et al. |
| 6,878,847 B2 | 4/2005 | Kasuga et al. |
| 6,888,024 B2 | 5/2005 | Dieterle et al. |
| 6,921,836 B1 | 7/2005 | Hibst et al. |
| 6,965,046 B2 * | 11/2005 | Paparizos ............. C07C 253/26 558/324 |
| 7,071,140 B2 | 7/2006 | Paparizos et al. |
| 7,348,291 B2 * | 3/2008 | Paparizos ........... B01J 23/8878 558/321 |
| 7,365,041 B2 * | 4/2008 | Miyaki ................ B01J 23/8892 502/319 |
| 7,473,666 B2 * | 1/2009 | Yanagi ................ B01J 23/8876 558/321 |
| 7,635,786 B2 | 2/2009 | Shin et al. |
| 7,579,501 B2 | 8/2009 | Teshigahara et al. |
| 7,632,777 B2 | 12/2009 | Teshigahara et al. |
| 7,638,458 B2 | 12/2009 | Shin et al. |
| 7,649,111 B2 * | 1/2010 | Liang .................... B01J 21/02 502/211 |
| 7,732,367 B2 * | 6/2010 | Stevenson ............ B01J 27/199 502/305 |
| 7,943,710 B2 | 5/2011 | Shin et al. |
| 7,999,133 B2 * | 8/2011 | Stevenson ............ B01J 27/188 562/533 |
| 8,153,546 B2 | 4/2012 | Brazdil et al. |
| 8,247,344 B2 | 8/2012 | Shin et al. |
| 8,258,073 B2 | 9/2012 | Besecker et al. |
| 8,350,075 B2 | 1/2013 | Brazdil et al. |
| 8,354,482 B2 | 1/2013 | Shin et al. |
| 8,361,923 B2 | 1/2013 | Kano et al. |
| 8,420,566 B2 | 4/2013 | Brazdil et al. |
| 8,455,388 B2 | 6/2013 | Brazdil et al. |
| 8,686,194 B2 | 4/2014 | Macht et al. |
| 9,199,921 B2 | 12/2015 | Endo et al. |
| 9,211,527 B1 | 12/2015 | Brazdil et al. |
| 9,346,036 B2 | 5/2016 | Yoshida et al. |
| 9,358,528 B2 | 6/2016 | Brazdil et al. |
| 9,364,817 B2 * | 6/2016 | Yoshida ................... B01J 37/04 |
| 9,815,045 B2 | 11/2017 | Lugmair et al. |
| 9,844,769 B2 | 12/2017 | Brazdil et al. |
| 10,137,437 B2 | 11/2018 | Sokolovskii et al. |
| 10,479,759 B2 | 11/2019 | Li et al. |
| 10,479,760 B2 | 11/2019 | Lugmair et al. |
| 10,626,082 B2 | 4/2020 | Brazdil et al. |
| 10,682,631 B2 | 6/2020 | Amakawa et al. |
| 10,780,427 B2 | 9/2020 | Brazdil et al. |
| 10,894,247 B2 | 1/2021 | Yang et al. |
| 10,940,463 B2 | 3/2021 | Iitsuka et al. |
| 11,433,383 B2 | 9/2022 | Aiki et al. |
| 2001/0051589 A1 | 12/2001 | Van Berge et al. |
| 2002/0198398 A1 | 12/2002 | Paparizos et al. |
| 2004/0063398 A1 | 4/2004 | Hechler et al. |
| 2005/0187406 A1 | 8/2005 | Kang et al. |
| 2005/0245623 A1 | 11/2005 | Van Berge et al. |
| 2006/0155139 A1 | 7/2006 | Yanagi et al. |
| 2006/0199730 A1 * | 9/2006 | Seely ................... C07C 253/26 502/246 |
| 2010/0076208 A1 | 3/2010 | Dhingra et al. |
| 2011/0092757 A1 | 4/2011 | Akagishi et al. |
| 2011/0237753 A1 | 9/2011 | Brazdil et al. |
| 2012/0130112 A1 | 5/2012 | Brazdil et al. |
| 2013/0023699 A1 | 1/2013 | Macht et al. |
| 2015/0238939 A1 | 8/2015 | Yoshida et al. |
| 2015/0367329 A1 | 12/2015 | Lim et al. |
| 2016/0051967 A1 | 2/2016 | Sokolovskii et al. |
| 2016/0175817 A1 * | 6/2016 | Brazdil .................... C07C 45/35 558/324 |
| 2017/0114007 A1 | 4/2017 | Brazdil et al. |
| 2018/0133699 A1 * | 5/2018 | Brazdil ................ B01J 23/8871 |
| 2018/0222850 A1 | 8/2018 | Li et al. |
| 2018/0222851 A1 | 8/2018 | Lugmair et al. |
| 2018/0318803 A1 | 11/2018 | Fukuzawa et al. |
| 2019/0001309 A1 * | 1/2019 | Fukuzawa ............ C07C 253/26 |
| 2019/0076829 A1 | 3/2019 | Sprenger et al. |
| 2021/0070693 A1 | 3/2021 | Morii et al. |

(56) References Cited

U.S. PATENT DOCUMENTS

| | | | |
|---|---|---|---|
| 2022/0001361 A1 | 1/2022 | Kim et al. | |
| 2022/0002233 A1 | 1/2022 | Kang et al. | |
| 2022/0023837 A1 | 9/2022 | Kang et al. | |
| 2022/0395817 A1 | 12/2022 | Kim et al. | |
| 2023/0373908 A1* | 11/2023 | Ryou | B01J 23/002 |

FOREIGN PATENT DOCUMENTS

| | | | |
|---|---|---|---|
| CN | 110214054 A | 9/2019 | |
| CN | 110248730 A | 9/2019 | |
| EP | 3974058 A1 | 3/2022 | |
| JP | S47013313 U | 10/1972 | |
| JP | S55056839 A | 4/1980 | |
| JP | S57171437 A | 10/1982 | |
| JP | S60-166037 A | 8/1985 | |
| JP | H0747271 A | 2/1995 | |
| JP | 2000037631 A | 2/2000 | |
| JP | 2002526241 A | 8/2002 | |
| JP | 2006521916 A | 9/2006 | |
| JP | 2010240593 A | 10/2010 | |
| JP | 2005313167 A | 8/2011 | |
| JP | 2013527141 A | 6/2013 | |
| JP | 2013169482 A | 9/2013 | |
| JP | 2016120468 A | 7/2016 | |
| JP | 2016520418 A | 7/2016 | |
| JP | 6124883 B2 | 5/2017 | |
| JP | 2018-140326 A | 9/2018 | |
| JP | 2022512791 A | 2/2022 | |
| KR | 1020050098270 A | 10/2005 | |
| KR | 10-0687671 B1 | 3/2007 | |
| KR | 10-0977358 B1 | 8/2010 | |
| KR | 10-2012-0021858 A | 3/2012 | |
| KR | 10-2013-007625 A | 1/2013 | |
| KR | 10-2015-0046224 A | 4/2015 | |
| KR | 10-1537459 B1 | 7/2015 | |
| KR | 10-2016-0066922 A | 6/2016 | |
| KR | 10-2016-0083698 A | 7/2016 | |
| KR | 10-2017-0007947 A | 1/2017 | |
| KR | 10-2017-0139602 A | 12/2017 | |
| WO | 2004078344 A1 | 9/2004 | |
| WO | 2011-119203 A1 | 9/2011 | |
| WO | 2014169163 | 10/2014 | |
| WO | 2014051090 A1 | 8/2016 | |
| WO | 2017130909 A1 | 8/2017 | |
| WO | 2018148158 A1 | 8/2018 | |
| WO | 2018148240 A1 | 8/2018 | |
| WO | 2019187786 A1 | 10/2019 | |

OTHER PUBLICATIONS

Binh et al., "Ammoxidation of Acrolein to Acrylonitrile Over Bismuth Molybdate Catalysts", Applied Catalysis A General, vol. 520 (2016), pp. 7-12.

* cited by examiner

[Fig. 1]
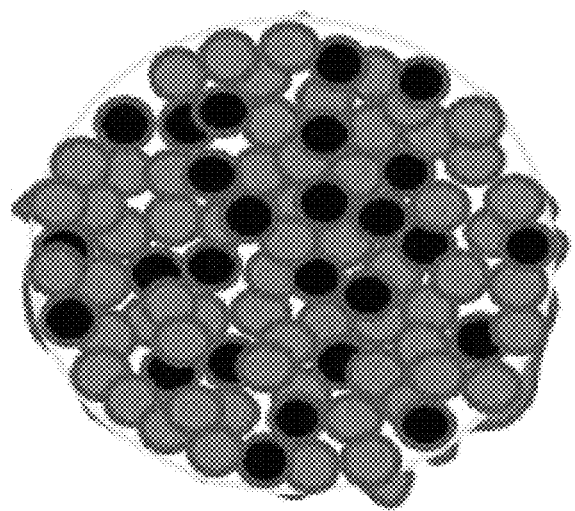
[Fig. 2]
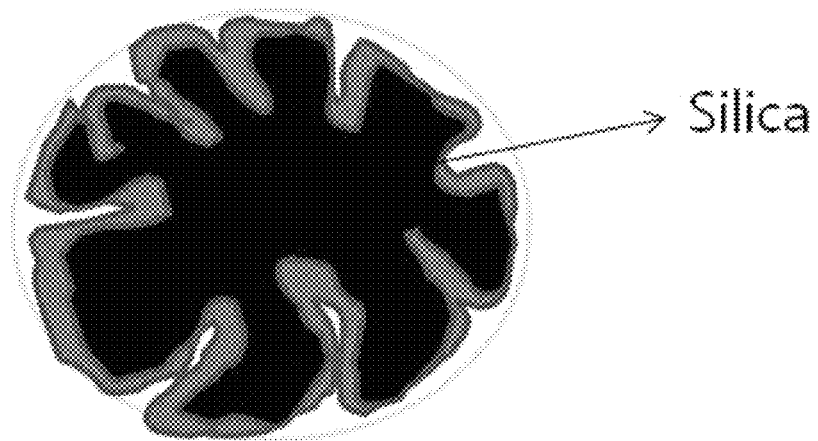

AMMOXIDATION CATALYST FOR PROPYLENE, MANUFACTURING METHOD OF THE SAME CATALYST, AMMOXIDATION METHOD USING THE SAME CATALYST

The present application is a National Phase entry pursuant to 35 U.S.C. § 371 of International Application No. PCT/KR2020/013098 filed on Sep. 25, 2020, and claims priority to and the benefit of Korean Patent Application No. 10-2019-0121172 filed on Sep. 30, 2019, Korean Patent Application No. 10-2019-0134089 filed on Oct. 25, 2019, and Korean Patent Application No. 10-2020-0123874 filed on Sep. 24, 2020 with the Korean Intellectual Property Office, the disclosures of which are herein incorporated by reference in their entirety.

FIELD

This invention relates to an ammoxidation catalyst for propylene, a manufacturing method of the same, and an ammoxidation method using the same.

BACKGROUND

An ammoxidation process of propylene is based on a mechanism of reduction in which ammonia and propylene are reacted and reoxidized, and in order to increase conversion of the reactant (namely, propylene) and selectivity and yield of the reaction product (namely acrylonitrile), catalysts of various compositions have been studied.

Specifically, since a Mo(molybdenum)-Bi(bismuth) oxide catalyst has been suggested, in order to increase the catalytic activity and stability, catalysts to which metals of various oxidation states are added have been studied. As the result, the yield of acrylonitrile was improved compared to the initial studies, according to the kind or amount of added metals.

However, despite diversification of catalyst compositions, due to insufficient studies on the structure and properties, remarkable increase in the conversion of the reactant (namely, propylene) and selectivity of the reaction product (namely, acrylonitrile) during the ammoxidation of propylene was limited.

Specifically, in general, metal precursors of aimed compositions and nano silica sol are coprecipitated, and then, spray dried and calcined, thus obtaining a catalyst of a secondary particle structure in which metal oxide particles and silica particles are agglomerated.

According to this method, secondary particles having a wide particle size distribution are obtained, thus requiring a classification process as a post-treatment. Furthermore, since the catalyst of the secondary particle structure is vulnerable to friction, it may be abraded or damaged during propylene ammoxidation in a fluidized bed reactor, and the catalyst should be continuously resupplied.

It is an object of the invention to provide an ammoxidation catalyst for propylene in which not only the external surface part (namely, the surface of a catalyst) but also the internal surface (pores) can participate in reactions, and to prepare acrylonitrile with higher yield by using such a catalyst.

SUMMARY

Specifically, according to one embodiment of the invention, there is provided an ammoxidation catalyst for propylene having a structure in which metal oxide of a specific composition is supported in a silica carrier, and having uniform particle size distribution in the supported state.

The catalyst of one embodiment has wide effective surface area capable of participating in reactions, and thus, has high catalytic efficiency and reactivity, and simultaneously, has small fine powder content, without passing through a classification process, and exhibits uniform particle size distribution.

Thus, using the catalyst of one embodiment, propylene can be converted with higher rate, and acrylonitrile can be prepared with higher selectivity and yield.

BRIEF DESCRIPTION OF THE DRAWINGS

FIG. 1 is a schematic illustration showing the catalyst prepared using coprecipitation and spray drying.

FIG. 2 is a schematic illustration showing the catalyst according to one embodiment.

DETAILED DESCRIPTION

Although various modifications can be made to the invention and the invention may have various forms, specific examples will be illustrated and explained in detail below. However, it should be understood that these are not intended to limit the invention to specific disclosure, and that the invention includes all modifications, equivalents or replacements thereof without departing from the spirit and technical scope of the invention. In explanation of the invention, in case it is judged that specific explanations regarding related known technologies may obscure the subject matter of the invention, those explanations will be omitted.

And, terms including ordinal numbers such as "a first", "a second" and the like are used to explain various constructional elements, but the constructional elements are not limited by these terms. These terms are used only to distinguish one constructional element from other constructional elements. For example, the first constructional element may be named as the second constructional element, and similarly, the second constructional elements may be also named as the first constructional elements, without departing from the scope of the right of the invention.

A singular expression includes a plural expression thereof, unless it is expressly stated or obvious from the context that such is not intended. As used herein, the terms "comprise" or "have", etc. are intended to designate the existence of practiced characteristic, number, step, constructional element or combinations thereof, and they are not intended to preclude the possibility of existence or addition of one or more other characteristics, numbers, steps, constructional elements or combinations thereof.

Hereinafter, "particle diameter Dv" means a particle diameter at v % point in cumulative volume distribution according to particle diameter. Namely, D50 is a particle diameter at 50% point in the cumulative volume distribution according to particle diameter, D90 is a particle diameter at 90% point in cumulative volume distribution according to particle diameter, and D10 is a particle diameter at 10% point in cumulative volume distribution according to particle diameter Hereinafter, an ammoxidation catalyst for propylene according to one embodiment will be explained in detail with reference to drawings.

An Ammoxidation Catalyst for Propylene

According to one embodiment of the invention, there is provided an ammoxidation catalyst for propylene in which metal oxide represented by the following Chemical Formula 1 is supported on a silica carrier,
wherein the catalyst has
D50 particle diameter of 30 to 300 μm, and
D10 particle diameter, D50 particle diameter and D90 particle diameter satisfying the relationship of the following Formula 1:

$$(D90-D10)/D50<2.0 \quad \text{(Formula 1)}$$

$$Mo_{12}Bi_aFe_bA_cB_dC_eO_x \quad \text{[Chemical Formula 1]}$$

in the Chemical Formula 1,
A is one or more elements of Ni, Mn, Co, Zn, Mg, Ca, and Ba,
B is one or more elements of Li, Na, K, Rb, and Cs,
C is one or more elements of Cr, W, B, Al, Ca, and V,
a to e, and x are respectively fractions of each atom or atomic group, and a is 0.1 to 5, b is 0.1 to 5, c is 0.01 to 10, d is 0.01 to 2, e is 0 to 10, and x is 24 to 48.

Commonly known propylene ammoxidation catalysts are prepared by coprecipitation and spray drying, and provided as a secondary particle structure in which metal oxide nanoparticles and silica nanoparticles are agglomerated (FIG. 1).

Since metal oxide particles are uniformly distributed inside and outside, but parts capable of participating in propylene ammoxidation reactions are limited to the external surface parts (namely, the surfaces of secondary particles), and a small surface area is provided, the amount of ammonia detached from the catalyst surface during the propylene ammoxidation reaction is large. On the contrary, since the catalyst of one embodiment is prepared by impregnation, it may be provided as a structure wherein metal oxide is supported on a silica carrier (FIG. 2).

For example, a silica carrier may be impregnated in a metal precursor solution by immersing the silica carrier in the metal precursor solution prepared such that stoichiometric mole ratio of metal oxide aimed is satisfied.

Thereafter, if a solvent (namely, water) is removed by drying, the metal precursor may remain on the pore walls of the silica carrier, and the metal precursor may be oxidized during a calcination process to form a film continuously coating the pore walls of the silica carrier.

The catalyst of one embodiment thus prepared, even if a classification process is not performed as post treatment after preparation, may have smaller fine powder content and improved durability relative to a catalyst prepared with the same composition by coprecipitation and spray drying. And, by controlling the composition of the metal oxide so as to further include metals forming active sites for a propylene ammoxidation reaction, as well as Mo and Bi known to increase the activity of an ammoxidation reaction, the catalytic activity may be further increased. Particularly, in the catalyst of one embodiment, by uniformly supporting the metal oxide in the internal pores of the silica carrier, parts capable of participating in a propylene ammoxidation reaction may be extended to the internal surfaces (pores) as well as to the external surface part (namely, the surface of the catalyst).

Moreover, the catalyst of one embodiment may be realized as a structure in which metal oxide is supported on a silica carrier, using impregnation, and it may have small fine particle content without passing through a classification process, and exhibit a uniform particle size distribution.

Furthermore, due to the structure in which the metal oxide is supported on a carrier and uniform particle size distribution, excellent attrition resistance may be exhibited, and thus, without resupplying a catalyst during propylene ammoxidation in a fluidized bed reactor, acrylonitrile may be prepared with higher yield.

Hereinafter, the catalyst of one embodiment will be explained in detail.

Structure of a Catalyst

The catalyst of one embodiment may have a structure comprising a silica carrier comprising second pores; an internal coating layer that continuously coats the wall surfaces of the second pores, and comprises metal oxide represented by Chemical Formula 1; and first pores positioned inside of the second pores, and occupying empty spaces except the internal coating layer. Specifically, the catalyst of one embodiment may have an egg-shell structure.

For this purpose, a silica carrier comprising a non-porous core part; and a porous shell part positioned on the surface of the non-porous core, and comprising second pores; may be used.

More specifically, the porous shell comprises depressed parts and protruded parts of the surface, wherein the depressed parts may be formed by opening of the second pores toward the surface of the porous shell.

Thus, the catalyst of one embodiment may have a structure comprising a coating layer that continuously coats the depressed and protruded parts of the porous shell, and comprises metal oxide represented by Chemical Formula 1; and first pores occupying empty spaces except the coating layer, in the depressed parts of the silica carrier.

The catalyst of one embodiment may have uniform particle size distribution to D50, and small fine powder content, when the metal oxide is supported on a silica carrier.

Specifically, the catalyst of one embodiment may have D50 particle diameter of 30 to 200 μm, and the ratio of [difference between D90 particle diameter and D10 particle diameter] to the D50 particle diameter may be less than 2.0, thus exhibiting a narrow particle diameter distribution.

More specifically, the catalyst of one embodiment may have D50 particle diameter of 30 μm or more, 35 μm or more, 40 μm or more, or 45 μm or more, and 300 μm or less, 280 μm or less, 260 μm or less, 240 μm or less, 220 μm or less, or 200 μm or less.

And, the catalyst of one embodiment may have a ratio of [difference between D90 particle diameter and D10 particle diameter] to D50 particle diameter of less than 2.0, 1.9 or less, 1.8 or less, 1.7 or less, 1.6 or less, or 1.5 or less, thus exhibiting narrow particle size distribution.

Namely, the uniformity of particle size distribution of the catalyst of one embodiment may be supported by the relationship of D10 particle diameter and D90 particle diameter to D50 particle diameter satisfying Formula 1, specifically Formula 1-1:

$$(D90-D10)/D50<2.0 \quad \text{(Formula 1)}$$

$$(D90-D10)/D50\leq1.5 \quad \text{(Formula 1-1)}$$

Attrition Loss of a Catalyst

Attrition of particles refers to a phenomenon in which solid particles are decomposed through mechanical or chemical processes. Attrition of particles is classified into abrasion and fragmentation, and both may occur simultaneously.

Particularly, catalyst particles may be attrited and micronized during a fluidized bed process, and thus, it is required to continuously resupply a catalyst in the attrited amount, which may have an influence on the economic efficiency of the whole process. As a standard for measuring attrition of particles, the ASTM9797-00 method is known. It is a method of measuring attrition loss using the following Formula, by filling 50 g of a catalyst (W0) in a vertical inner tube having an inner diameter of 35 mm and a height of 710 mm, flowing $N_2$ gas at 10 L/min, and then, measuring the amount of catalyst (W) collected in a fine powder filter after 5 hours.

Attrition loss (%)=(W0)/W×100

The catalyst of one embodiment has attrition loss measured according to the ASTM9797-00 method, of 9% or less, 8.7% or less, 8.4% or less, 8.2% or less, or 8% or less, and thus, the loss amount is very small, and attrition resistance is excellent. Thus, compared to a catalyst of a secondary particle structure prepared through coprecipitation and spray drying, the catalyst of one embodiment exhibits excellent attrition resistance, and without additional supply of a catalyst during propylene ammoxidation in a fluidized bed reactor, and acrylonitrile may be prepared with higher yield.

Composition of Metal Oxide

Meanwhile, even if a catalyst has the same structure as the catalyst of one embodiment, if the kind and content of the components constituting the metal oxide do not satisfy Chemical Formula 1, active sites formed may be insufficient for propylene ammoxidation or have excessively high density.

Thus, the kind and content of the components constituting the metal oxide should satisfy Chemical Formula 1.

Particularly, when the metal oxide is represented by Chemical Formula 1-1, due to synergistic effects of increasing movement speed of Fe, molybdenum, and lattice oxygen to increase conversion, increasing partial oxidation reaction property of propylene due to the formation of complex oxide of Co and molybdenum, and dispersing the active sites of complex oxide including K and molybdenum to increase acrylonitrile selectivity, the activity in a propylene ammoxidation reaction may be further increased:

$Mo_{12}Bi_aFe_bCo_cK_dO_x$ (Chemical Formula 1)

In the Chemical Formula 1-1,
a to d, and x are respectively fractions of each atom or atomic group, and a may be 0.1 to 5, specifically 0.1 to 2.0, b may be 0.1 to 5, specifically 0.5 to 3.0, c may be 0.01 to 10, specifically 1 to 10, d may be 0.01 to 2, specifically 0.01 to 1.0, and x may be 24 to 48, specifically 28 to 45.

Weight Ratio of Metal Oxide:Silica Carrier

The catalyst of one embodiment may comprise the metal oxide and the silica carrier at a weight ratio of 10:90 to 15:95, specifically 20:80 to 50:50, for example 15:85 to 35:65 (metal oxide:silica carrier).

Within this range, the catalyst of one embodiment may have high activity and high selectivity of acrylonitrile.

A Method for Preparing an Ammoxidation Catalyst for Propylene

According to another embodiment of the invention, there is provided a method for preparing the catalyst of one embodiment as explained above using impregnation.

As briefly explained above, the catalyst of one embodiment may be prepared by the processes of supporting a metal precursor solution in the silica carrier using impregnation, drying, and then calcining. More specifically, the method for preparing the catalyst of one embodiment comprises the steps of:

preparing a first precursor solution comprising additives of citric acid, oxalic acid or a mixture thereof; and a Mo precursor, preparing a second precursor solution comprising a Bi precursor, a Fe precursor, an A precursor (A=one or more elements of Ni, Mn, Co, Zn, Mg, Ca, and Ba), and a B precursor (B=one or more elements of Li, Na, K, Rb, and Cs), mixing the first and second precursor solutions such that the molar ratio of metals satisfies stoichiometric molar ratio of the following Chemical Formula 1, supporting the mixture of the first and second precursor solutions in a silica carrier, drying the silica carrier in which the mixture of the first and second precursor solutions is supported, and calcining the dried material:

$Mo_{12}Bi_aFe_bA_cB_dC_eO_x$ [Chemical Formula 1]

in the Chemical Formula 1,
A is one or more elements of Ni, Mn, Co, Zn, Mg, Ca, and Ba,
B is one or more elements of Li, Na, K, Rb, and Cs,
C is one or more elements of Cr, W, B, Al, Ca, and V, and
a to e, and x are respectively fractions of each atom or atomic group, and a is 0.1 to 5, b is 0.1 to 5, c is 0.01 to 10, d is 0.01 to 2, e is 0 to 10, and x is 24 to 48.

A Preparation Process of the First Precursor Solution

The step of preparing a first precursor solution may comprise dissolving a Mo precursor and additives in water at 20 to 80° C. to prepare an aqueous solution comprising water, a Mo precursor and additives.

In the step of preparing the first precursor solution, additives including citric acid, oxalic acid, or a mixture thereof are used.

In the catalyst preparation processes using coprecipitation and spray drying, these additives function as a strength control agent. While in the above one embodiment, these additives function for making the first precursor solution transparent.

When adding the additives, the weight ratio of the molybdenum precursor and the additives may be controlled to satisfy a ratio of 1:0.1 to 1:1, specifically 1:0.2 to 1:0.7, and within this range, solubility of the molybdenum precursor may be increased, but it is not limited thereto.

A Preparation Process of the Second Precursor Solution

A second solution comprising metal precursors, other than the Mo precursor included in the first precursor solution may be prepared.

Specifically, the step of preparing the second precursor solution may include preparing a second precursor solution essentially comprising a Bi precursor, a Fe precursor, an A precursor, and a B precursor, and optionally, further comprising a C precursor (one or more elements of Cr, W, B, Al, Ca, and V), in water at 20 to 50° C.

More specifically, in the step of preparing the second precursor solution, considering the composition of metal oxide in the desired catalyst, the kinds of metal precursors other than Mo precursor may be selected.

For example, considering the composition of metal oxide satisfying the Chemical Formula 1-1, a second precursor solution comprising water, a Bi precursor, a Fe precursor, a Co precursor, and a K precursor may be prepared.

The processes of preparing the first and second precursor solutions are independent from each other, and the preparation sequence is not limited.

A Process for Supporting a Mixture of the First and Second Precursor Solutions in a Carrier After mixing the first and second precursor solutions, the mixture may be supported on a silica carrier. Wherein, the mixture of the first and second precursor solutions may be supported in the first pores in the silica carrier, by introducing the silica carrier comprising second pores as explained above in the mixture of the first and second precursor solutions. Specifically, a silica carrier in which the metal oxide is not supported may have D50 of 20 to 400 μm.

More specifically, a silica carrier in which the metal oxide is not supported may have D50 of 20 to 400 μm; and comprise second pores having a diameter of 10 to 200 nm.

More specifically, D50 of the silica carrier in which the metal oxide is not supported may be 20 μm or more, 25 μm or more, 30 μm or more, 35 μm or more, 40 μm or more, or 43 μm or more, and 400 μm or less, 350 μm or less, 300 μm or less, 270 μm or less, 230 μm or less, or 200 μm or less.

And, the diameter of the second pores included in the silica carrier in which the metal oxide is not supported may be 10 nm or more, 15 nm or more, or 20 nm or more, and 200 nmor less, 100 nm or less, 50 nm or less, 40 nm or less, or 30 nm or less.

A Process of Drying a Carrier in which the Mixture of the First and Second Precursor Solutions is Supported The process of drying the silica carrier in which the mixture of the first and second precursor solutions is supported may comprise the steps of: first vacuum drying the silica support in which a mixture of the first and second precursor solutions is supported at 120 to 160 mbar, and second vacuum drying the first vacuum dried material at 30 to 50 mbar, to obtain a silica carrier in which a mixture of the first and second precursor solutions is supported.

Specifically, by conducting the first vacuum drying at 60 to 80° C. for 1 to 2 hours, and conducting the second vacuum drying at 80 to 100° C. for 15 to 45 minutes, the solvent (namely, water) may be removed, and only the first and second precursors may remain on the wall surfaces of the first pores.

Although the second vacuum dried material may be immediately calcined, by third drying at atmospheric pressure, even the solvent (namely, water) remaining after the second vacuum drying may be effectively removed.

Specifically, the third drying may be conducted at 100 to 120° C. for 20 to 30 hours.

However, these are no more than examples, and drying conditions are not specifically limited as long as a carrier in which the first and second precursors are supported may be obtained.

Final Calcination Process

Finally, the dried material, namely, a carrier in which the first and second precursors are supported may be calcined at 500 to 700° C. for 2 to 5 hours to finally obtain a catalyst.

However, the drying and calcinations conditions are no more than examples, and any conditions may be sufficient as long as the solvents may be sufficiently removed from the internal pores of the carrier, and metal precursor may be oxidized.

Ammoxidation Method of Propylene

According to yet another embodiment of the invention, there is provided a method for ammoxidation of propylene, comprising a step of reacting propylene and ammonia in the presence of the catalyst of the one embodiment, as explained above, in a reactor.

The catalyst of one embodiment has high activity and high temperature stability, and may be used for propylene ammoxidation reaction to increase conversion of propylene, and selectivity and yield of acrylonitrile.

For the details other than the catalyst of one embodiment, matters commonly known in the art may be referred to, and the detailed explanations thereof are omitted.

Hereinafter, embodiments of the invention will be explained in more detail in the following examples. However, these examples are presented only as the illustrations of the invention, and the scope of the invention is not limited thereby.

EXAMPLES

Example 1

(1) A Preparation Process of a Precursor Solution

In distilled water at 60° C., 10.592 g of a Mo precursor $((NH_4)_6Mo_7O_{24})$ and 0.1 g of citric acid were introduced, and mixed to prepare a Mo precursor solution.

Separately, in distilled water at room temperature, 1.819 g of a Bi precursor($Fe(NO_3)_3 \cdot 5H_2O$), 9.488 g of a Co precursor($Co(NO_3)_2 \cdot 6H_2O$), 2.990 g of a Fe precursor($Fe(NO_3)_2 \cdot 9H_2O$), and 0.354 g of a K precursor($KNO_3$) were introduced, and 1.46 g of nitric acid ($HNO_3$) was added, and then, they were mixed to prepare a mixed solution of Bi, Fe, Co, and K precursors.

The Mo precursor solution; and the mixed solution of Bi, Fe, Co, and K precursors were mixed to complete a mixed solution of Mo, Bi, Fe, Co, and K precursors.

In the mixed solution of precursors, the total amount of distilled water was 36.59 g.

(2) A Process of Supporting a Precursor Solution on a Silica Carrier (Using Impregnation)

Silica ($SiO_2$, D60-60A, AGC-Si) particles having D50 particle diameter of 55 μm, and internal pore size of 24.4 nm were used as a carrier.

In the mixed solution of Mo, Bi, Fe, Co, and K precursors, the silica carrier was introduced, and the solution was stirred sequentially at room temperature and 80° C., respectively for 2 hours, such that the mixed solution of Mo, Bi, Fe, Ni, Co, and K precursors was sufficiently supported in the internal pores of the silica carrier.

(3) Processes of Drying and Calcination of a Silica Carrier in which a Precursor Solution is Supported Thereafter, the silica carrier on which the mixed solution of Bi, Fe, Co, and K precursors was supported was recovered and introduced in a rotary vacuum dryer, and then, first vacuum dried under pressure of 140 mbar and temperature of 70° C. for 1 hour and 40 minutes, and second vacuum dried under pressure of 40 mbar and temperature of 90° C. for 30 minutes.

The second vacuum dried material was recovered and introduced into an oven, and dried a third time under atmospheric pressure and temperature of 110° C. for 24 hours, and then, while maintaining a temperature of 580° C. in a box calcination furnace of air atmosphere, heat treated for 3 hours to finally obtain a catalyst of Example 1.

(4) A Process of Propylene Ammoxidation

In a tubular reactor having an inner diameter of ⅜ inches, 0.05 g of quartz wool was charged for activation of a catalyst, and 0.2 g of the catalyst of Example 1 was charged in the reactor.

The internal pressure of the reactor charged with quartz wool and catalyst was maintained at atmospheric pressure (1 atm), and while raising the internal temperature of the reactor at 10° C./min, nitrogen and ammonia gas were flowed as pretreatment. After the internal temperature of the reactor reached 400° C. at which an ammoxidation reaction can be progressed, it was maintained under reducing gas atmosphere for 15 minutes so as to achieve sufficient pretreatment.

While supplying air together with reactants of propylene and ammonia in the pretreated reactor, an ammoxidation process of propylene was conducted. Wherein, the amounts of the reactants supplied were such that a volume ratio became propylene:ammonia:air=0.8:1.2:8, and the total weight hourly space velocity (WHSV) of propylene, ammonia and air became 1.54 $h^{-1}$.

After the ammoxidation reaction was completed, the product was recovered, and in order to confirm whether acrylonitrile was sufficiently produced, it was analyzed using various apparatuses.

The analysis method, analysis results, and the like will be explained in detail in Experimental Examples below.

Examples 2 to 7

(1) A Preparation Process of a Catalyst (Using Impregnation)

Each catalyst of Examples 2 to 7 was prepared by the same method as Example 1, except that a precursor solution was prepared according to the composition described in the following Table 1, and a silica carrier described in the following Table 2 was used.

(2) An Ammoxidation Process of Propylene

An ammoxidation process of propylene was conducted using each catalyst of Examples 2 to 7 instead of Example 1, and then, the product was recovered, and analyzed by the same method as Example 1.

Comparative Example 1

(1) A Preparation Process of a Catalyst (Coprecipitation and Spray Drying)

First, in distilled water at 60° C., 10.592 g of a Mo precursor($(NH_4)_6Mo_7O_{24}$) and 3.18 g of citric acid were introduced and mixed to prepare a Mo precursor solution.

Separately, in distilled water at room temperature, 1.819 g of a Bi precursor($Fe(NO_3)_3 \cdot 5H_2O$), 9.488 g of a Co precursor($Co(NO_3)_2 \cdot 6H_2O$), 2.990 g of a Fe precursor($Fe(NO_3)_2 \cdot 9H_2O$), and 0.354 g of a K precursor($KNO_3$) were introduced, and 0.83 g of nitric acid ($HNO_3$) was added, and then, they were mixed to prepare a mixed solution of Bi, Fe, Co, and K precursors.

The Mo precursor solution; and the mixed solution of Bi, Fe, Co, and K precursors were mixed, and 22.530 g of silica sol (LUDOX AS 40, solid content: 40%) was added thereto, and the mixture was stirred, and then, spray dried under conditions of 120° C. (inlet) and 230° C. (outlet) using a disk-type spray dryer.

The obtained powders were calcined at 580° C. for 3 hours to finally obtain a catalyst of Comparative Example 1.

(2) An Ammoxidation Process of Propylene

An ammoxidation process of propylene was conducted by the same method as Example 1, except that the catalyst of Comparative Example 1 was used instead of the catalyst of Example 1.

After the ammoxidation reaction of Comparative Example 1 was finished, the product was recovered, and analyzed by the same method as Example 1.

Comparative Examples 2 to 4

(1) A Preparation Process of a Catalyst (Impregnation)

Catalysts of Comparative Examples 2 to 4 were respectively prepared by the same method as Example 1, except that a precursor solution was prepared according to the composition described in the following Table 1, and a silica carrier described in the following Table 2 was used.

(2) An Ammoxidation Process of Propylene

An ammoxidation process of propylene was conducted using each catalyst of Comparative Examples 2 to 4 instead of the catalyst of Example 1, and then, the product was recovered and analyzed by the same method as Example 1.

Comparative Example 5

(1) A Preparation Process of a Catalyst (Using Impregnation)

In distilled water at 60° C., 10.592 g of a Mo precursor ($(NH_4)_6Mo_7O_{24}$) and 0.53 g of citric acid were introduced, and mixed to prepared a Mo precursor solution.

Separately, in distilled water at room temperature, 1.091 g of Bi precursor($Fe(NO_3)_3 \cdot 5H_2O$), 4.365 g of Co precursor ($Co(NO_3)_2 \cdot 6H_2O$), 3.636 g of Fe precursor($Fe(NO_3)_2 \cdot 9H_2O$), 2.908 g of Ni precursor($Ni(NO_3)_2 \cdot 6H_2O$), 0.045 g of K precursor($KNO_3$), 1.954 g of Ce precursor($Ce(NO_3)_3 \cdot 6H_2O$), 2.564 g of Mg precursor($Mg(NO_3)_2 \cdot 6H_2O$), and 0.037 g of Rb precursor($RbNO_3$) were introduced, and 0.74 g of nitric acid ($HNO_3$) was added, and then, they were mixed to prepare a mixed solution of Bi, Co, Fe, Ni, K, Ce, Mg, and Rb precursors.

The Mo precursor solution; and the mixed solution of Bi, Co, Fe, Ni, K, Ce, Mg, and Rb precursors were mixed to complete a mixed solution of Mo, Bi, Fe, Co, and K.

In the mixed solution of precursors, the total amount of distilled water was 18.45 g.

(2) An Ammoxidation Process of Propylene

An ammoxidation process of propylene was conducted using the catalyst of Comparative Example 5 instead of the catalyst of Example 1, and then, the product was recovered and analyzed by the same method as Example 1.

TABLE 1

| | Mo precursor solution | | Heterogeneous metal precursor solution | | | | | | |
|---|---|---|---|---|---|---|---|---|---|
| | Citric acid | Mo | Bi | Co | Fe | K | Nitric acid | Distilled water | $SiO_2$ |
| Example 1 | 3.18 | 10.592 | 1.819 | 9.488 | 2.990 | 0.354 | 1.46 | 36.59 | 18.30 |
| Example 2 | 3.18 | 10.592 | 2.425 | 6.403 | 2.020 | 0.177 | 2.03 | 50.68 | 25.34 |
| Example 3 | 3.18 | 10.592 | 2.425 | 6.403 | 2.020 | 0.177 | 1.37 | 34.30 | 17.15 |
| Example 4 | 3.18 | 10.592 | 2.910 | 6.257 | 3.030 | 0.025 | 1.41 | 35.35 | 17.68 |
| Example 5 | 3.18 | 10.592 | 1.819 | 9.488 | 2.990 | 0.354 | 1.46 | 36.59 | 18.30 |
| Example 6 | 3.18 | 10.592 | 1.819 | 9.488 | 2.990 | 0.354 | 1.46 | 36.59 | 18.30 |
| Example 7 | 3.18 | 10.592 | 1.819 | 9.488 | 2.990 | 0.354 | 1.46 | 36.59 | 18.30 |
| Comp. Ex. 1 | 3.18 | 10.592 | 1.819 | 9.488 | 2.990 | 0.354 | 0.83 | 20.65 | 22.53 (40% Silica sol) |

TABLE 1-continued

| | Mo precursor solution | | Heterogeneous metal precursor solution | | | | | | |
|---|---|---|---|---|---|---|---|---|---|
| | Citric acid | Mo | Bi | Co | Fe | K | Nitric acid | Distilled water | SiO$_2$ |
| Comp. Ex. 2 | 3.18 | 10.592 | 1.819 | 9.488 | 2.990 | 0.354 | 2.03 | 50.68 | 18.30 |
| Comp. Ex. 3 | 3.18 | 10.592 | 1.819 | 9.488 | 2.990 | 0.354 | 2.03 | 50.68 | 18.30 |
| Comp. Ex. 4 | 0.93 | 3.089 | 16.977 | | | 0.000 | 1.46 | 36.52 | 18.26 |

In Table 1, Mo is $(NH_4)_6Mo_7O_{24}$, Bi is $Bi(NO_3)_3 \cdot 5H_2O$, Co is $Co(NO_3)_2 \cdot 6H_2O$, Fe is $Fe(NO_3)_2 \cdot 9H_2O$, and K is $KNO_3$. And, the omitted unit is g.

Meanwhile, Comparative Example 5 wherein many materials were added to a heterogeneous metal precursor solution was omitted in Table 1 for convenience.

TABLE 2

| | | Catalyst construction | | | |
|---|---|---|---|---|---|
| | Preparation method | Content and composition of active material(metal oxide) | | Content of Carrier | |
| | | | | carrier | Product name |
| Example 1 | impregnation | 33 wt % $(Mo_{12}Bi_{0.75}Fe_{1.48}Co_{6.52}K_{0.7}O_x)$ | | 67 wt % | D60-60A(AGC-Si) |
| Example 2 | impregnation | 25 wt % $(Mo_{12}Bi_{1.0}Fe_{1.0}Co_{4.4}K_{0.35}O_x)$ | | 75 wt % | D110-60A(AGC-Si) |
| Example 3 | impregnation | 33 wt % $(Mo_{12}Bi_{0.82}Fe_{0.8}Co_{6.4}K_{0.5}O_x)$ | | 67 wt % | D60-60A(AGC-Si) |
| Example 4 | impregnation | 33 wt % $(Mo_{12}Bi_{1.2}Fe_{1.5}Co_{4.3}K_{0.05}O_x)$ | | 67 wt % | D60-60A(AGC-Si) |
| Example 5 | impregnation | 33 wt % $(Mo_{12}Bi_{0.75}Fe_{1.48}Co_{6.52}K_{0.7}O_x)$ | | 67 wt % | D60-60A(AGC-Si) |
| Example 6 | impregnation | 33 wt % $(Mo_{12}Bi_{0.75}Fe_{1.48}Co_{6.52}K_{0.7}O_x)$ | | 67 wt % | D110-60A(AGC-Si) |
| Example 7 | impregnation | 33 wt % $(Mo_{12}Bi_{0.75}Fe_{1.48}Co_{6.52}K_{0.7}O_x)$ | | 67 wt % | D300-60A(AGC-Si) |
| Comp. Ex. 1 | spray drying | 50 wt % $(Mo_{12}Bi_{0.75}Fe_{1.48}Co_{6.52}K_{0.7}O_x)$ | | 50 wt % | LUDOX-AS40 |
| Comp. Ex. 2 | impregnation | 33 wt % $(Mo_{12}Bi_{0.75}Fe_{1.48}Co_{6.52}K_{0.7}O_x)$ | | 67 wt % | D60-60A(AGC-Si) |
| Comp. Ex. 3 | impregnation | 33 wt % $(Mo_{12}Bi_{0.75}Fe_{1.48}Co_{6.52}K_{0.7}O_x)$ | | 67 wt % | D300-60A(AGC-Si) |
| Comp. Ex. 4 | impregnation | 33 wt % $(Bi_2O_{3.3} \cdot _0MoO_3)$ | | 67 wt % | D60-60A(AGC-Si) |
| Comp. Ex. 5 | impregnation | 33 wt % $(Mo_{12}Bi_{0.45}Ce_{0.90}Fe_{1.8}Ni_{2.0}Co_{3.0}Mg_{2.0}K_{0.09}Rb_{0.05}O_n)$ | | 67 wt % | D60-60A(AGC-Si) |

Experimental Example 1: Catalyst Analysis

According to the following analysis method, each catalyst of Examples and Comparative Examples was analyzed, and the results were shown in Table 3:

Measurement of D10, D50 and D90: Dv may be measured using a laser diffraction method. Specifically, particle size distribution is calculated by introducing each catalyst of Examples and Comparative Examples in a particle size measuring device (Microtrac, Blue wave) using laser diffraction, and measuring diffraction pattern difference according to particle size when particles pass through laser beam. By calculating particle diameter at 10%, 50% and 90% points in cumulative volume distribution according to particle diameter, D10, D50 an D90 can be measured, and particle size distribution ((D90-D10)/D50 value) may be output.

Attrition loss: According to ASTM9797-00, 50 g of the catalyst (WO) was filled in a vertical inner tube having an inner diameter of 35 mm and a height of 710 mm, N2 gas was flowed at 10 L/min, and after 5 hours, the amount of the catalyst (W) collected in a fine powder filter was measured, and attrition loss was measured using the following Formula.

$$\text{Attrition loss (\%)} = (W - W0)/W$$

TABLE 3

| | Prep. method | Content and composition of active material (metal oxide) | D50 of carrier | D50 of catalyst | (D90 − D10)/D50 | Attrition loss |
|---|---|---|---|---|---|---|
| Example 1 | Impreg. | 33 wt % $(Mo_{12}Bi_{0.75}Fe_{1.48}Co_{6.52}K_{0.7}O_x)$ | 55 μm | 66 μm | 0.75 | 5.3% |
| Example 2 | Impreg. | 25 wt % $(Mo_{12}Bi_{1.0}Fe_{1.0}Co_{4.4}K_{0.35}O_x)$ | 110 μm | 115 μm | 0.54 | 4.2% |
| Example 3 | Impreg. | 33 wt % $(Mo_{12}Bi_{0.82}Fe_{0.8}Co_{6.4}K_{0.15}O_x)$ | 50 μm | 56 μm | 0.68 | 5.6% |
| Example 4 | Impreg. | 33 wt % $(Mo_{12}Bi_{1.2}Fe_{1.5}Co_{4.3}K_{0.05}O_x)$ | 55 μm | 66 μm | 0.45 | 2.3% |
| Example 5 | Impreg. | 33 wt % $(Mo_{12}Bi_{0.75}Fe_{1.48}Co_{6.52}K_{0.7}O_x)$ | 24 μm | 30 μm | 1.32 | 7.9% |
| Example 6 | Impreg. | 33 wt % $(Mo_{12}Bi_{0.75}Fe_{1.48}Co_{6.52}K_{0.7}O_x)$ | 130 μm | 150 μm | 0.98 | 5.3% |
| Example 7 | Impreg. | 33 wt % $(Mo_{12}Bi_{0.75}Fe_{1.48}Co_{6.52}K_{0.7}O_x)$ | 185 μm | 200 μm | 1.45 | 6.5% |
| Comp. Ex. 1 | spray drying | 50 wt % $(Mo_{12}Bi_{0.75}Fe_{1.48}Co_{6.52}K_{0.7}O_x)$ | 20 μm | 30 μm | 2.73 | 10.8% |
| Comp. Ex. 2 | Impreg. | 33 wt % $(Mo_{12}Bi_{0.75}Fe_{1.48}Co_{6.52}K_{0.7}O_x)$ | 14 μm | 18 μm | 3.40 | 32% |
| Comp. Ex. 3 | Impreg. | 33 wt % $(Mo_{12}Bi_{0.75}Fe_{1.48}Co_{6.52}K_{0.7}O_x)$ | 300 μm | 320 μm | 4.45 | 10.3% |
| Comp. Ex. 4 | Impreg. | 33 wt % $(Bi_2O_{3.3} \cdot _0MoO_3)$ | 55 μm | 83 μm | 5.40 | 23% |
| Comp. Ex. 5 | Impreg. | 33 wt % $(Mo_{12}Bi_{0.45}Ce_{0.90}Fe_{1.8}Ni_{2.0}Co_{3.0}Mg_{2.0}K_{0.09}Rb_{0.05}O_n)$ | 55 μm | 75 μm | 2.10 | 9.2% |

Since the catalysts of Comparative Examples were prepared by coprecipitation and spray drying, they exhibit wide particle size distribution, requiring a classification process as post-treatment. Specifically, the catalysts of Comparative Examples have (D90-D10)/D50 values of 2 or more.

On the contrary, since the catalysts of Examples were prepared by the processes of immersing a metal precursor solution in a silica carrier and then removing the solvent and calcining, they exhibit uniform particle size distribution without a separate classification process. Specifically, the catalysts of Examples have (D90−D10)/D50 values of 1.5 or less, specifically 1.0 or less.

According to Table 3, it can be seen that compared to coprecipitation and spray drying used for preparing the catalyst of Comparative Example 1, impregnation used for preparing the catalysts of Examples 1 to 7 is favorable for the preparation of a catalyst having excellent attrition loss with uniform particle size.

Wherein, since the catalyst of Comparative Example 1 was prepared through coprecipitation and spray drying, it exhibits wide particle size distribution requiring a post-treatment (for example, classification). On the contrary, since the catalysts of Examples 1 to 7 were prepared through impregnation, they exhibit uniform particle size distribution without a separate classification process. Meanwhile, although the catalysts of Comparative Examples 2 and 3 were prepared through impregnation, D50 particle diameters do not meet the ranges specified in one embodiment (namely, 30 to 200 μm), and thus, particle size distribution and attrition loss are inferior even compared to Comparative Example 1.

Specifically, it is inferred that since Comparative Example 2 used a carrier having excessively small D50 particle diameter, active components were insufficiently impregnated in the carrier having small particle diameter, and thus, D50 particle diameter of the final catalyst did not reach the lower limit of the range specified in one embodiment, and particle size distribution and attrition loss became inferior.

And, it is inferred that since Comparative Example 3 used a carrier having excessively large D50 particle diameter, active components were non-uniformly impregnated in the carrier having large particle diameter, and thus, D50 particle diameter of the final catalyst exceeded the upper limit of the range specified in one embodiment, and particle size distribution and attrition loss became inferior.

On the other hand, although the catalysts of Comparative Examples 4 and 5 were prepared through impregnation and D50 particle diameters meet the range specified in one embodiment (namely, 30 to 200 μm), due to the influence of active metals, particle size distribution and attrition loss are equivalent or inferior to Comparative Example 1.

In the case of Comparative Example 4, it is inferred that due to the influence of metal oxide comprising only Mo and Bi as active metals, active components were insufficiently impregnated in the carrier, rendering the particle size distribution and attrition loss of the final catalyst inferior.

And, in the case of Comparative Example 5, it is inferred that due to the inclusion of many active metals (namely, Ce, Fe, Ni, Co, Mg, K, and Rb) as well as Mo and Bi as active metals, active components were non-uniformly impregnated in the carrier, and thus, the particle size distribution and attrition loss remained equivalent to Comparative Example 1.

Experimental Example 2: Analysis of Propylene Ammoxidation Product

Using Gas chromatography (Manufacturing company: Agilent Device name: HP 6890 N) equipped with FID (Flame Ionization Detector and TCD (Thermal conductivity detector), each ammoxidation product of Examples and Comparative Examples was analyzed.

Specifically, with FID, products including ethylene, hydrogen cyanide, acetaldehyde, acetonitrile, acrylonitrile, and the like were analyzed, and with TCD, gas products including $NH_3$, $O_2$, CO, $CO_2$, and the like and unreacted propylene were analyzed, thus calculating the mole number of reacted propylene and the mole number of ammoxidation product in Examples and Comparative Examples.

The analysis results and the mole number of supplied propylene were substituted in the following Formulas 1, 2 and 3, thus calculating conversion of propylene, selectivity and yield of acrylonitrile, which is the ammoxidation reaction product of propylene, and the calculation values were described in the following Table 4:

Conversion of propylene (%)=100*(mole number of ammoxidation of reacted propylene)/(mole number of supplied propylene)    (Formula 1)

Selectivity of acrylonitrile (%)=100*(mole number of produced acrylonitrile)/(mole number of reacted propylene)    (Formula 2)

Yield of acrylonitrile (%)=100*(mole number of produced acrylonitrile)/(mole number of supplied propylene)    (Formula 3)

TABLE 4

| | | | Analysis results of propylene ammoxidation product | | |
|---|---|---|---|---|---|
| | (D90 − D10)/D50 | Attrition loss | conversion of propylene(%) | selectivity of acrylonitrile(%) | Yield of acrylonitrile (%) |
| Example 1 | 0.75 | 5.3% | 61 | 77 | 47 |
| Example 2 | 0.54 | 4.2% | 56 | 72 | 40 |
| Example 3 | 0.68 | 5.6% | 68 | 77 | 52 |
| Example 4 | 0.45 | 2.3% | 73 | 79 | 58 |
| Example 5 | 1.32 | 7.9% | 62 | 73 | 45 |
| Example 6 | 0.98 | 5.3% | 53 | 68 | 36 |
| Example 7 | 1.45 | 6.5% | 47 | 65 | 31 |
| Comp. Ex. 1 | 2.73 | 10.8% | 25 | 37 | 9 |
| Comp. Ex. 2 | 3.40 | 32% | 62 | 48 | 30 |
| Comp. Ex. 3 | 4.45 | 10.3% | 38 | 45 | 17 |
| Comp. Ex. 4 | 5.40 | 23% | 8 | 44 | 3.5 |
| Comp. Ex. 5 | 2.10 | 9.2% | 43 | 54 | 23 |

Since the catalyst of Comparative Example 1 was prepared through coprecipitation and spray drying, internal pores are scarcely included, and thus, parts capable of participating in reactions are limited to the external surface parts.

Moreover, since the catalyst of Comparative Example 1 has non-uniform particle size distribution, if it is applied for a propylene ammoxidation process without classification, catalytic efficiency and reactivity may be low. And, since the catalyst of Comparative Example 1 has a secondary particle structure vulnerable to friction, it may be attrited or damaged during the progress of propylene ammoxidation in a fluidized bed reactor. Thus, unless additional catalyst is continuously resupplied during the reaction, conversion of propylene and yield of acrylonitrile may inevitably decrease.

Practically, according to Table 2, it is confirmed that when the reaction was progressed using the catalyst of Comparative Example 1 without resupply of the catalyst during the reaction, conversion of propylene was 25% and yield of acrylonitrile was just 9%. Meanwhile, the catalysts of Comparative Examples 2 to 5 have particle size distribution and attrition loss equivalent or inferior to Comparative Example 1, but due to the structures prepared by impregnation, they have wider effective surface areas capable of participating in the reactions than the catalyst of Comparative Example 1, and thus, conversion of propylene and yield of acrylonitrile may be improved compared to Comparative Example 1.

However, the catalysts of Comparative Examples 2 and 3 do not meet the D50 particle diameter and particle size distribution specified in one embodiment (namely, D50 particle diameter: 30 to 200 μm, particle size distribution: (D90-D10)/D50<2.0), and thus, have lower conversion of propylene and yield of acrylonitrile compared to Examples 1 to 7.

And, since the catalyst of Comparative Example 4 does not meet the particle size distribution specified in one embodiment (namely, particle size distribution: (D90-D10)/D50<2.0), and comprises only Mo and Bi as active metals, conversion of propylene and yield of acrylonitrile are inferior to Examples 1 to 7.

Since the catalyst of Comparative Example 5 does not meet the particle size distribution specified in one embodiment (namely, particle size distribution: (D90-D10)/D50<2.0), and comprises Ce, Fe, Ni, Co, Mg, K, and Rb as well as Mo and Bi as active metals, thus forming active sites of excessively high density, it has inferior conversion of propylene and yield of acrylonitrile compared to Examples 1 to 7.0n the other hand, it is shown that the catalysts of Examples 1 to 7, due to the structures prepared by impregnation, have wider effective surface areas capable of participating in the reactions than the catalyst of Comparative Example 1, and meet the D50 particle diameter and particle size distribution specified in one embodiment (namely, D50 particle diameter: 30 to 200 μm, particle size distribution: (D90-D10)/D50<2.0), and the composition of metal oxide meets the above explained Chemical Formula 1, and thus, conversion of propylene and yield of acrylonitrile are remarkably improved.

Referring to the catalysts of Examples 1 to 7, by controlling D50 particle diameter and particle size distribution of a catalyst, composition of metal oxide, and the like within the ranges specified in one embodiment, it is also possible to further improve conversion of propylene and yield of acrylonitrile.

The invention claimed is:

1. An ammoxidation catalyst for propylene in which metal oxide represented by Chemical Formula 1-1 is supported on a silica carrier,
    wherein the silica carrier has D50 of 20 to 400 μm,
    wherein the catalyst has
    D50 particle diameter of 30 to 300 μm, and
    D10 particle diameter, D50 particle diameter and D90 particle diameter satisfying the relationship of the following Formula 1:

$(D90-D10)/D50<2.0$     (Formula 1)

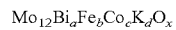     (Chemical Formula 1-1)

wherein in the Chemical Formula 1-1, a is 0.1 to 5, b is 0.1 to 5, c is 0.01 to 10, d is 0.01 to 2, and x is 24 to 48.

2. The ammoxidation catalyst for propylene according to claim 1, wherein the catalyst comprises
    the silica carrier comprising first pores;
    an internal coating layer that coats wall surfaces of the first pores, and comprises the metal oxide represented by the Chemical Formula 1-1; and
    second pores positioned inside of the first pores, and occupying empty spaces except the internal coating layer.

3. The ammoxidation catalyst for propylene according to claim 1, wherein the catalyst has D50 particle diameter of 45 to 200 μm.

4. The ammoxidation catalyst for propylene according to claim 1, wherein the catalyst has D10 particle diameter, D50 particle diameter and D90 particle diameter satisfying the relationship of Formula 1-1:

$(D90-D10)/D50 \leq 1.5$.     (Formula 1-1)

5. The ammoxidation catalyst for propylene according to claim 1, wherein the weight ratio of the metal oxide and the silica carrier is 15:85 to 35:65.

6. The ammoxidation catalyst for propylene according to claim 1, wherein the catalyst has attrition loss of 9% or less, said attrition loss being calculated using the following Formula, by filling 50 g of the catalyst (WO) in a vertical inner tube having an inner diameter of 35 mm and a height of 710 mm, flowing $N_2$ gas at 10 L/min, and then, measuring the amount of the catalyst (W) collected in a fine powder filter, according to ASTM9797-00:

Attrition loss (%)=$(W-W0)/W$.

7. A method for preparing an ammoxidation catalyst for propylene of claim 1, comprising:
    preparing a first precursor solution comprising additives of citric acid, oxalic acid or a mixture thereof; and a Mo precursor,
    preparing a second precursor solution comprising a Bi precursor, a Fe precursor, a Co precursor, and a K precursor,
    mixing the first and second precursor solutions such that the molar ratio of metals satisfies stoichiometric molar ratio of Chemical Formula 1-1,
    supporting the mixture of the first and second precursor solutions on a silica carrier,
    drying the silica carrier in which the mixture of the first and second precursor solutions is supported, and
    calcining the dried material.

8. The method for preparing an ammoxidation catalyst for propylene according to claim 7, wherein in the first precursor solution, a weight ratio of the Mo precursor to additives is 1:0.1 to 1:1.

9. The method for preparing an ammoxidation catalyst for propylene according to claim 7, wherein drying the silica carrier in which a mixture of the first and second precursor solutions is supported comprises:
    a first vacuum drying of the silica support on which a mixture of the first and second precursor solutions is supported at 120 to 160 mbar, and a second vacuum drying of the first vacuum dried material at 30 to 50 mbar, to obtain a silica carrier on which a mixture of the first and second precursor solutions is supported.

10. The method for preparing an ammoxidation catalyst for propylene according to claim 9, wherein the first vacuum drying is conducted at 60 to 80° C.

11. The method for preparing an ammoxidation catalyst for propylene according to claim 9, wherein the second vacuum drying is conducted at 80 to 100° C.

12. The method for preparing an ammoxidation catalyst for propylene according to claim 9, further comprising a third drying the second vacuum dried material at atmospheric pressure.

13. The method for preparing an ammoxidation catalyst for propylene according to claim 12, wherein the third drying is conducted at 100 to 120° C.

14. The method for preparing an ammoxidation catalyst for propylene according to claim 7, wherein the calcining of the dried material is conducted at 500 to 700° C.

15. A method for ammoxidation of propylene, comprising a step of reacting propylene and ammonia in the presence of the catalyst of claim 1, in a reactor.

* * * * *